US005766149A

United States Patent [19]

Kriesel et al.

[11] Patent Number: 5,766,149

[45] Date of Patent: Jun. 16, 1998

[54] MIXING AND DELIVERY SYSTEM

[76] Inventors: Marshall S. Kriesel, 80 N. Mississippi Rd., Saint Paul, Minn. 55104; Thomas N. Thompson, 6300 Wentworth, Richfield, Minn. 55423

[21] Appl. No.: 606,082

[22] Filed: Feb. 23, 1996

[51] Int. Cl.[6] .................... A61M 37/00

[52] U.S. Cl. .................... 604/89; 604/82; 604/91; 604/92; 604/410

[58] Field of Search .................... 604/82, 83, 84, 604/89, 92, 91, 408, 410, 416, 903, 58

[56] References Cited

U.S. PATENT DOCUMENTS 4,950,237 8/1990 Henault et al. .................... 604/82

*Primary Examiner*—Michael Buiz

*Assistant Examiner*—N. Kent Gring

*Attorney, Agent, or Firm*—James E. Brunton

[57] ABSTRACT

An apparatus for separately storing a medicament component, such as a drug and for mixing this component with a liquid component, such as a sterilized diluent, to form a beneficial agent which can be delivered to a patient from the container containing the liquid component. The device includes a novel collapsible vial structure which can be used for controllably introducing a support structure carrying the medicament component into the liquid container whereby the medicament and liquid components will thoroughly mix under sterile conditions.

20 Claims, 3 Drawing Sheets

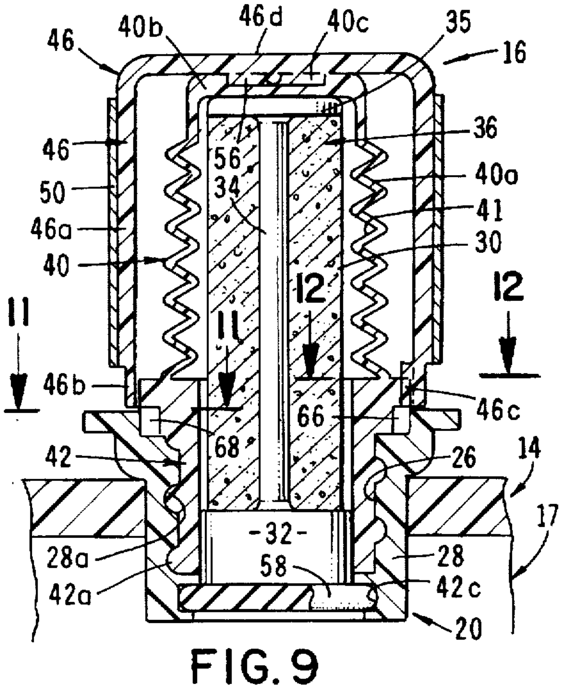
FIG. 9
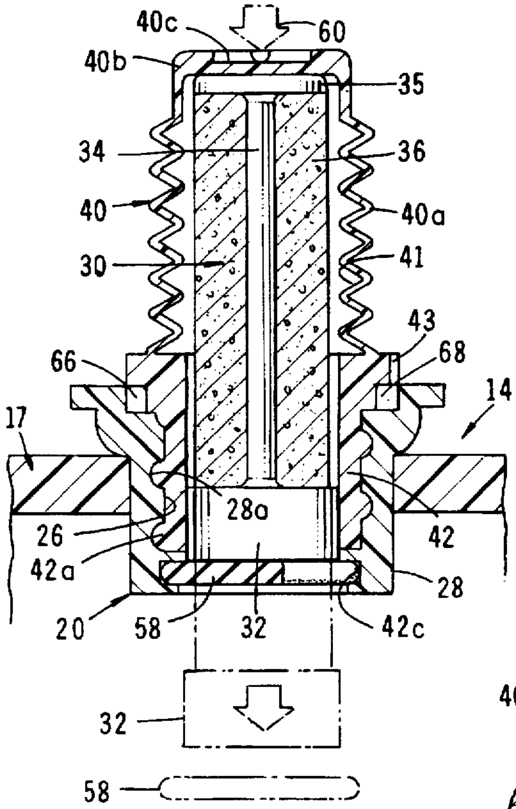
FIG. 10
FIG. 13
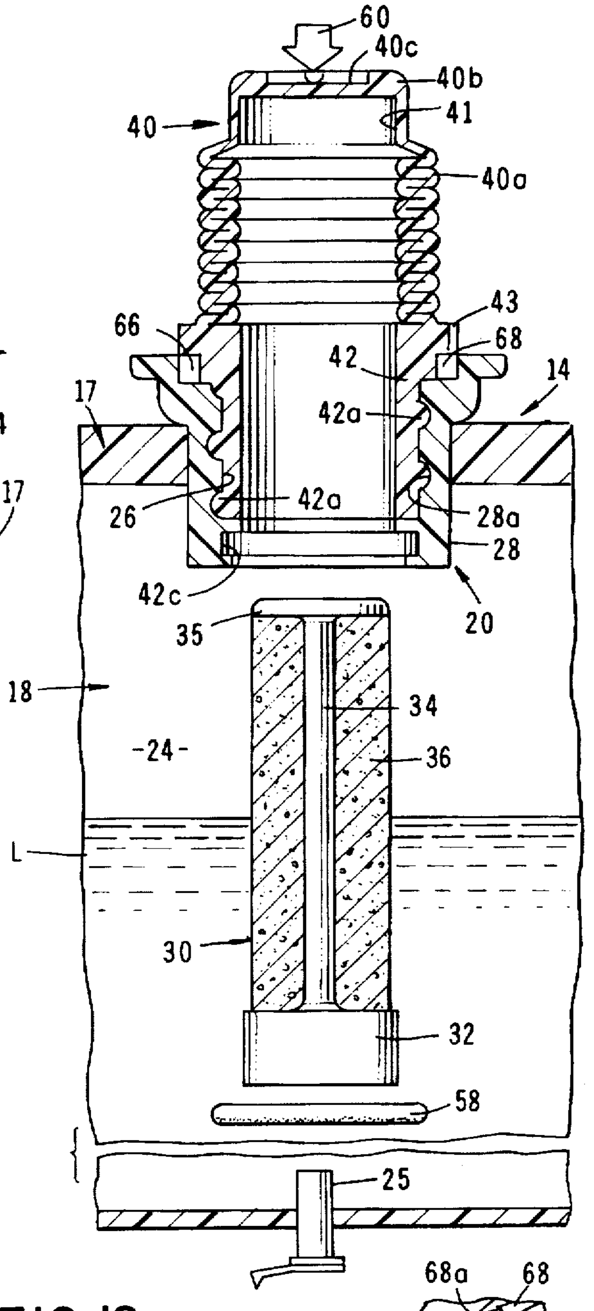
FIG. 12
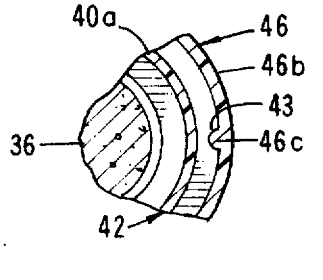
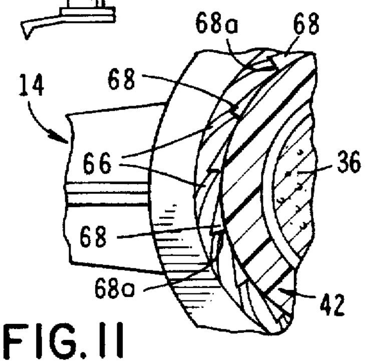
FIG. 11

MIXING AND DELIVERY SYSTEM

BACKGROUND OF THE INVENTION

1. Field of the Invention

The present invention relates generally to component mixing. More particularly, the invention concerns an improved apparatus for separately storing a first component, such as a drug and for mixing this first component with a second component, such as a sterilized diluent, to form a beneficial agent which can be delivered to a patient from the container containing the second component. The device includes novel means for interconnecting a container housing the first component with a flexible bag containing the second component and then for mixing the components under sterile conditions.

2. Discussion of the Invention

In the past, pharmaceuticals have been provided by drug manufacturers in sterilized vials, typically of glass construction. When the pharmaceuticals are in powder form, they are generally administered to the patient within a carrier liquid by standard intravenous procedures. Such carrier liquids include saline solution, dextrose solution and sterilized water.

Mixing of the powdered pharmaceuticals with the carrier liquid has been accomplished in several ways many of them being quite crude. For example, a common practice is to inject a quantity of the liquid carrier into the vial to dissolve the powdered component. Then using a cannula and syringe, the solution thus formed is injected into a larger container such as a flexbag containing the liquid carrier. This method is quite tedious and provides substantial opportunities for contamination and error.

In those instances where the pharmaceutical must be diluted before delivery to a patient, as is the case with powdered pharmaceuticals, the pharmaceutical can also be injected directly into a container of diluent and the container then interconnected with a suitable administration set for intravenous delivery of the solution to a patient. As a general rule, the diluent is packaged in glass bottles, or flexible plastic containers such as those sold under the names MINI-BAG™ and VIAFLEX® by Travenol Laboratories, Inc. of Deerfield, Illinois. These containers are conveniently provided with administration ports for connection to the administration set which delivers the container contents from the container to the patient. The pharmaceutical is typically added to the container through some type of an inlet port or vial receptacle provided on the container.

Because infusion of medicaments is most often accomplished in a hospital environment, it is the nurse, doctor or medical technician who mixes the drug and diluent usually at one time shortly before administration of the drug to the patient. This mixing step can be time consuming and hazardous, as for example, when toxic drugs are involved. Further, since many of the prior art mixing devices are crude and imprecise, accurate, sterile and thorough mixing of the drug and the diluent is most difficult and time consuming. Accordingly, such devices are not well suited for use in the home environment.

Several types of closed drug delivery systems which are somewhat more sophisticated have recently been made available. These systems typically comprise a flexible container such as a plastic bag to which a glass drug vial can be easily coupled. The flexible container usually contains a liquid diluent and often includes a frangible member that allows fluid passage only when broken. As a general rule, when the drug vial is coupled with the flexible container, the stopper of the drug vial is pierced and the frangible member ruptured so as to allow sterile communication between the drug vial and the liquid diluent contents of the flexible container. Mixing of the drug with the diluent is accomplished by manipulation of the flexible container. Exemplary of prior art systems of this character are those disclosed in U.S. Pat. No. 4,583,971 issued to Bocquet, et al. and in U. S. Pat. No. 4,606,734 issued to Lyons. The Lyons apparatus includes a compressible chamber with a liquid component therein, the compressible chamber including gas trapping and reservoir compartments in open communication. The gas trapping compartment can be connected to a container such as a drug vial having a mixing component therein. After a pathway between the vial and the gas trapping compartment is opened, mixing is accomplished through manipulation of the compressible chamber.

Another very successful prior art, dual container system is described in U.S. Pat. Nos. 4,614,267 issued to Larkin and 4,614,515 issued to Tripp and Larkin. In this system, a flexible diluent container includes a tubular port which provides means for securing thereto a stoppered medicament vial as well as a stopper removal means. The stopper removal means includes an engagement element, or extractor, which is attached to a removable cover and seals the inner end of the port. In use, as the vial is advanced into the tubular port, the vial stopper moves into engagement with the extractor which grips the stopper enabling it to be pulled from the vial as the cover is pulled from the port. Once the stopper has been removed from the vial, the powdered contents of the vial, such as a lyophilized drug, can be dumped into the diluent in the bag and mixed therewith through manipulation of the bag.

Still another type of component mixing device is disclosed in U.S. Pat. No. 4,467,588 issued to Carveth. The Carveth device includes two sealed chambers having a frangible sterilized connection therebetween. One chamber carries the liquid component and the other carries a sealed vial containing the second component. The frangible connection provides a sterile pathway for intermixing the components.

The devices of the present invention comprise improvements upon the devices disclosed in U.S. Pat. No. 5,385,545, 5,385,546, and 5,484,410 issued to the present inventors, and offer numerous advantages over the prior art devices by providing a closed system for separately storing and selectively intermixing a wide variety of different types of medicaments and other beneficial agents with a diluent or other parenteral fluid under completely sterile conditions. As will become apparent from the discussion which follows, the present application expands on the inventive concept set forth in the aforementioned patents. Accordingly, the patents, U.S. Pat. No. 5,385,545, 5,385,546, and 5,484,410 are hereby incorporated by reference as through fully set forth herein. These patents should be referred to to obtain a complete understanding of the extent of the novel improvements described herein. Reference should also be made to the patents for a definition of many of the terms used in the present application.

SUMMARY OF THE INVENTION

The apparatus of the present invention is used for intermixing first and second components and includes a flexible container having a fluid reservoir for containing a liquid component, such as a diluent. In fluid communication with the reservoir is an inlet port into which the assembly containing the first component, such as a beneficial agent, can be introduced. The assembly carrying the beneficial agent includes a support structure to which the beneficial agent is removably affixed and a housing, which serves to enclose the support structure within a sealed, sterile environment. The housing uniquely comprises an outer, easily removable, protective shield and an inner collapsible container within which the support structure and the beneficial agent are contained. At the desired time, after the assembly carrying the beneficial agent has been mated with the flexible container, the support structure along with the beneficial agent is introduced into the fluid reservoir of the flexible container. Once in the fluid reservoir, the beneficial agent will controllably separate, from the support structure and will thoroughly intermix with the fluid to form the solution made up of the liquid component and the beneficial agent to be delivered to the patient via an administration set that is connected to the flexible container.

It is an object of the present invention to provide an apparatus of the character described in the preceding paragraph which provides the opportunity to add to a diluent or other parenteral fluid contained within a flexible solution container (flexbag), selected elements, chemical compounds and biologically active materials, including drugs, medicaments, biological agents, and other therapeutic agents (additives).

Another object of the invention is to provide an apparatus of the character described in which the adding means, including the substrate which carries the first component, or additive, is maintained within a completely sterile environment until immediately prior to the controlled mixing of the first and second components.

Another object of the invention is to provide an apparatus of the class described in which a wide variety of selected additives can be removably affixed to the substrate that is controllably exposed to the liquid contained within the fluid reservoir of the flexbag assembly.

Another object of the invention is to provide a device of the aforementioned type in which toxic or other hazardous compounds, including those with short therapeutic lives can be separately and safely stored until immediately prior to their use following being intermixed with the liquid component contained within the separate flexible bag container.

Another object of the invention is to provide a device of the character described in the preceding paragraph in which toxic or other hazardous compounds which are to be intermixed with the liquid component can be separately and safely handled during the manufacture of the substrate portion of the device and in which the substrate carrying the hazardous materials can, following manufacture, b e safely stored until time of use.

Another object of the invention is to provide a device of the class described in which the beneficial agent is housed within a uniquely configured, collapsible vial, which upon being collapsed, causes the beneficial agent to be directly introduced into the fluid reservoir of t he flexbag.

Still another object of the invention is to provide a device of the character described in the preceding paragraphs which is easy to use, is highly reliable, and is inexpensive to produce in quantity so that the device can be disposed of after use.

BRIEF DESCRIPTION OF THE DRAWINGS

FIG. 9 is an enlarged front elevational, cross-sectional view of a portion of the apparatus of the invention showing the vial subassembly connected to the fluid container portion of the apparatus.

FIG. 10 is a cross-sectional view similar to FIG. 9 illustrating the additive injection step wherein the support assembly of the invention is introduced into the fluid reservoir of the fluid container or flex bag.

FIG. 11 is a cross-sectional view taken along lines 11-11 of FIG. 9.

FIG. 12 is a cross-sectional view taken along lines 12-12 of FIG. 9.

FIG. 13 is a cross-sectional, exploded view similar to FIG. 10 but showing the support assembly falling by force of gravity into the fluid reservoir of the flex bag.

DESCRIPTION OF THE INVENTION

Figure 1:
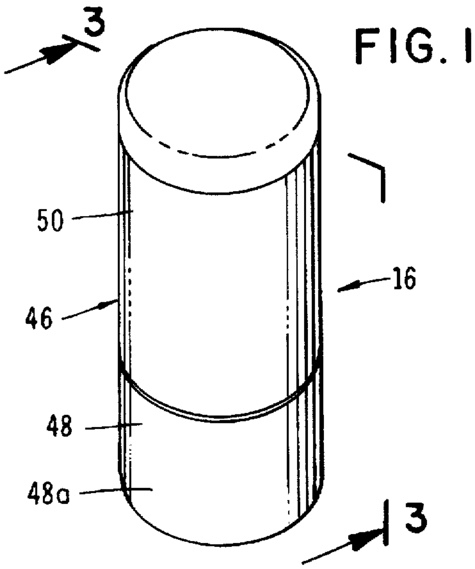
FIG. 1 is a generally perspective view of one form of the vial assembly of the apparatus of the present invention.
Figure 6:
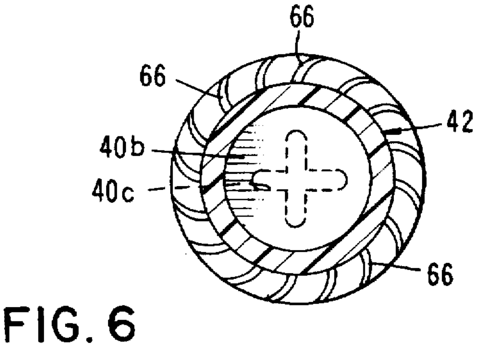
FIG. 6 is a view taken along lines 6—6 of FIG. 2.
Figure 7:
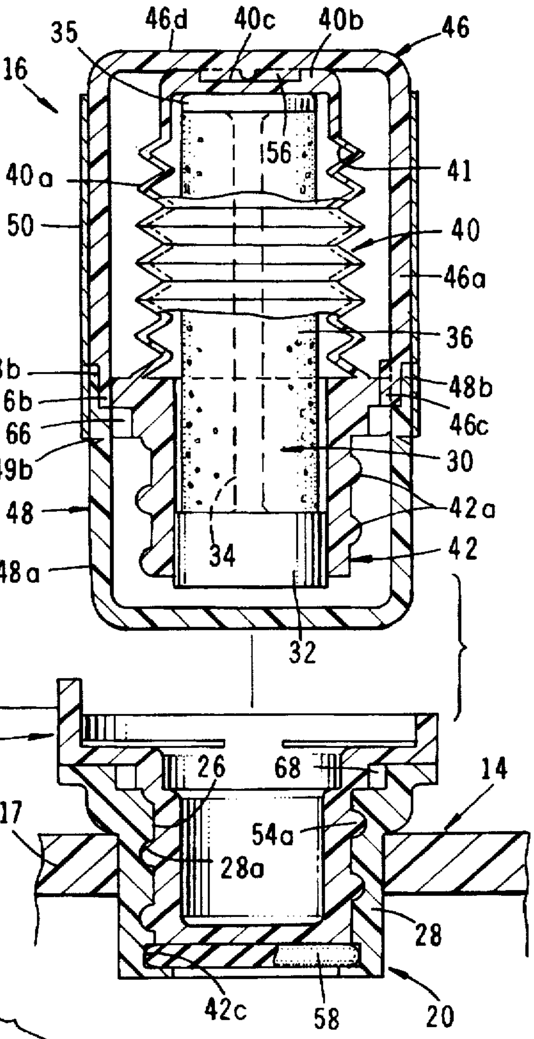
FIG. 7 is an enlarged, cross-sectional view of the vial assembly and of the inlet portion of the fluid container of one form of the apparatus of the invention as the components appear prior to mating.
Figure 8:
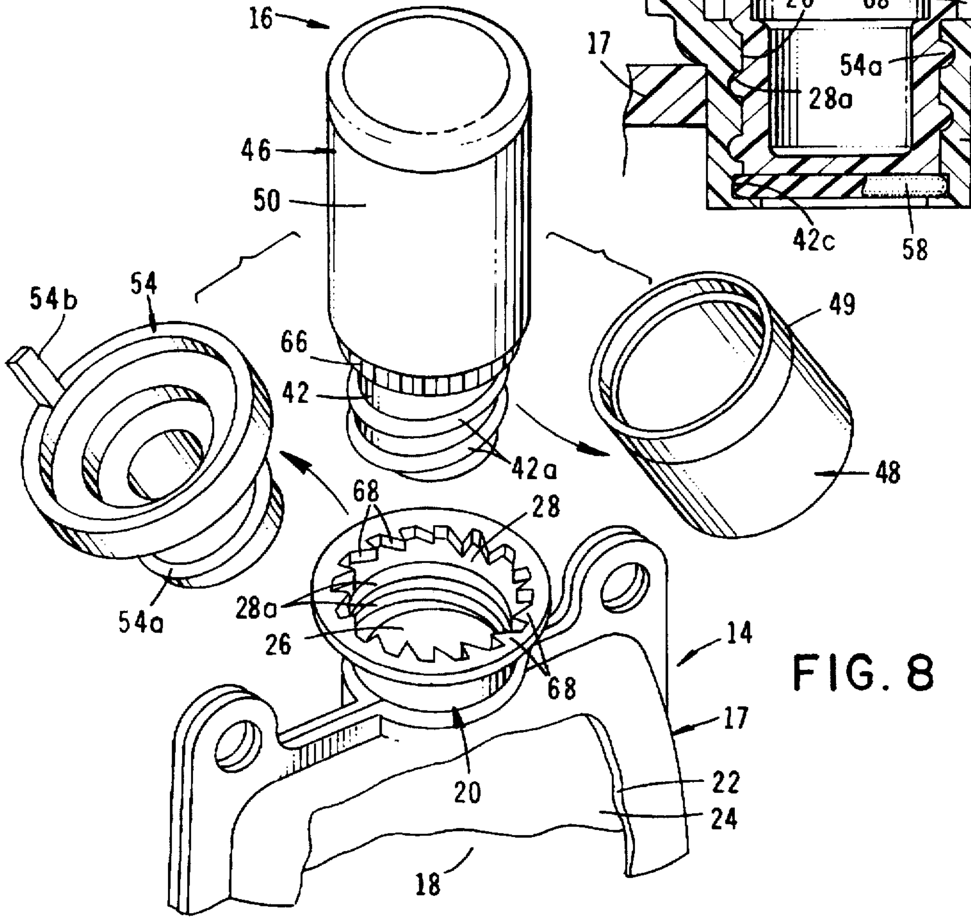
FIG. 8 is a generally perspective, exploded view of portions of the apparatus of the invention illustrating the manner of interconnection of the vial assembly with the fluid container of the apparatus.

Referring to the drawings and particularly to FIGS. 1 through 8, one form of the apparatus of the invention for controllably intermixing a first medicament component with the second liquid component is there shown. The apparatus here comprises two major assemblies, namely a container assembly 14 and a collapsible vial assembly 16 (FIGS. 1 and 8). Container assembly 14 includes a container 17 having a fluid reservoir 18 for containing a first component such as a parenteral fluid, and an inlet port 20 formed in the upper portion of the container (FIG. 8). Reservoir 18 is formed by sealably interconnected flexible walls 22 and 24 and inlet port 20 is formed at the lower end of a generally cylindrically shaped receiving chamber 26 which is superimposed over reservoir 18 and is in open communication therewith (FIG. 8). Walls 22 and 24, which cooperate to define reservoir 18, are suitably interconnected with a cylindrical wall 28, which defines receiving chamber 26 of the inlet port of container 14. As shown in FIG. 13, reservoir 18 is provided with a fluid outlet 25.

Figure 2:
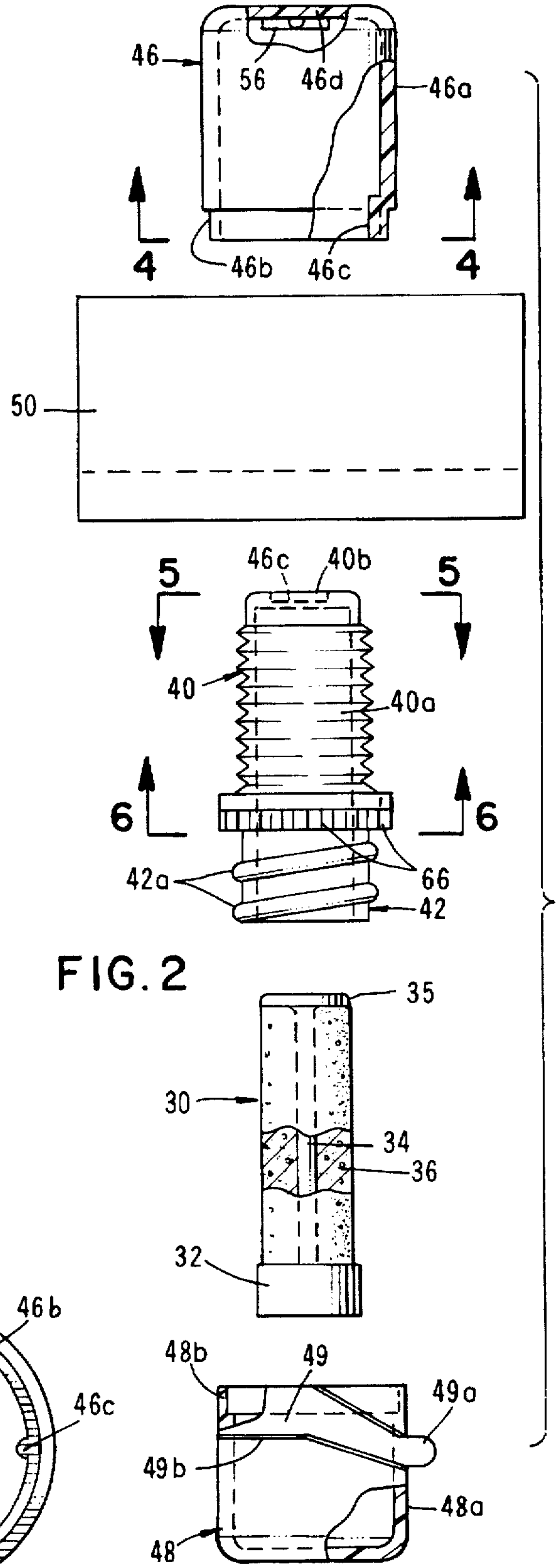
FIG. 2 is a front-elevational, exploded view, partially in cross section of the vial assembly shown in FIG. 1.

The apparatus of the present invention also comprises adding means, of the character more fully defined in U.S. Pat. 5,484,410, which is incorporated herein by reference. The adding means functions to present the medicament or second component to the first liquid component in a manner to permit intermixing the two components. In the embodiment of the invention shown in the drawings, the adding means comprises a support subassembly 30 (FIG. 2), which forms a part of the collapsible vial assembly 16, and includes a generally cylindrically shaped elastomeric, plug-like base 32 and a support column 34 one end of which is connected to plug 32. A top wall 35 is connected to the other end of column 34. As best seen in FIGS. 2 and 13, the second medicament component 36, which is generally annular in shape, surrounds column 34. Support assembly 30 is partially receivable within a collapsible container subassembly

40 of unique construction which also comprises a part of collapsible vial assembly 16.

Figure 3:
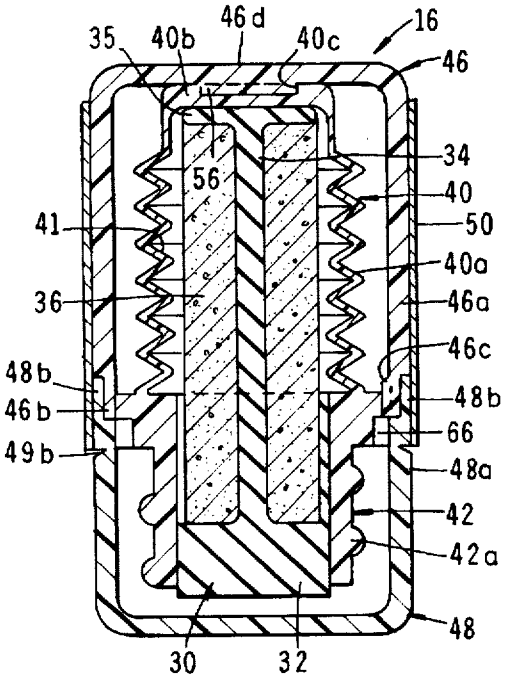
FIG. 3 is an enlarged, cross-sectional view taken along line s 3—3 of FIG. 1.

Turning particularly to FIG. 3, the collapsible vial assembly of the present form of the invention can be seen to further comprise a generally tubular shaped, externally threaded base 42 to which the bellows shaped wall 40*a* of the collapsible container subassembly 40 is connected. Cooperating with collapsible wall 40*a* to form an enclosure 41 is a closure wall 40*b* . Formed in closure wall 40*b* is a generally "X" shaped cavity 40*c* , the purpose of which will presently be described.

Figure 4:
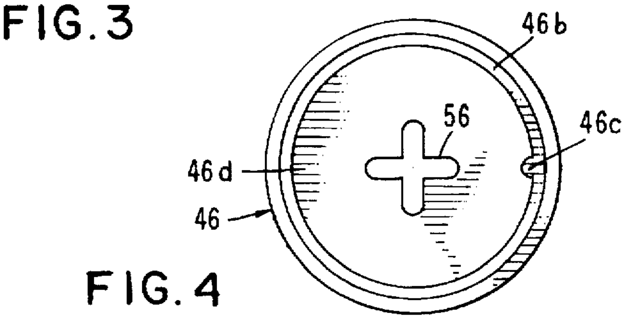
FIG. 4 is a view taken along lines 4—4 of FIG. 2.

To protect the collapsible vial 40, a hollow protective cap or cover 46 is receivable over collapsible vial 40 in the manner shown in FIG. 3. Protective cover 46 forms a part of the enclosure housing of the invention and includes a downwardly depending skirt 46*a* which is provided with a stepped lower extremity 46*b* of the character best seen in FIGS. 2 and 3. Formed on extremity 46*b* is a drive bead 46*c* , the purpose of which will presently be described (FIG. 4). Interconnected with protective cover 46 is a tear-away protective shield 48 which is receivable over base 42 of vial assembly 16. Protective shield 48 which includes the second part of the enclosure housing, also includes a skirt-like portion 48*a* which terminates in a stepped extremity 48*b* that is adapted to mate with stepped extremity 46*b* of protective cap 46 (FIG. 3).

As best seen in FIG. 2, protective shield 48 includes a spiral wound, frangible portion 49 which forms a part of skirt 48*a* . Portion 49 initially circumscribes a portion of threaded base 42 and is provided with an integral pull tab 49*a* which permits the spiral wound portion of the protective shield to be pulled from the lower skirt portion so as to expose step 46*b* of protective cover 46 and enable separation of protective shield 48 therefrom. To permit easy separation of frangible portion 49*a* a tear-line 49*b* circumscribes skirt-like portion 48*b* of the protective shield (FIG. 3).

As indicated in FIGS. 2 and 3, a tearable medicament label 50 surrounds cover 46 with the lower portion of the medicament label surrounding the step-like portion 48*b* of protective shield 48. Label 50 functions to securely join cover 46 and shield 48 until the frangible portion of the shield is removed by pulling on pull-tab 49*a*. As pull-tab 49*a* is pulled outwardly, the medicament label 50 will tear so as to expose step 46*b* of cover 46 and enable separation of protective shield 48 from the assemblage. Removal of shield 48 exposes threads 42*a* of base 42 and permits threadable mating of collapsible vial subassembly 40 with internal threads 28*a* provided on internal wall 28 of the inlet port of container 14 (FIG. 8).

As best seen in FIGS. 7 and 8, prior to use, the inlet port of container 14 is protected by a removable protective closure element 54 which is provided with external threads 54*a* that are adapted to initially mate with the internal threads 28*a* provided in the inlet port of container 17. Closure 54 remains in position within the inlet port of the container until immediately prior to mating the collapsible vial assembly 40 with the inlet port of the container 14. To simplify removal of closure member 54 from the inlet port, an upstanding gripping tab 54*b* is provided at the upper rim of the closure member 54.

Figure 5:
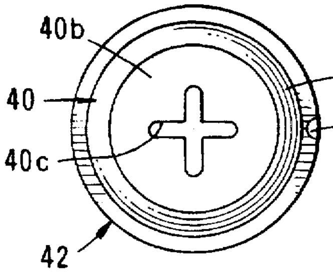
FIG. 5 is a view taken along lines 5—5 of FIG. 2.

When it is desired to intermix the medicament component 36 with the liquid component "L" contained within the flexbag container 17, the sterile closure member 54 is first removed from the container inlet port by grasping tab 54*b* and rotating member 54 counterclockwise relative to container 17. Next, protective shield 48 is removed from the vial assembly by grasping pull tab 49*a* and exerting an outward motion which tears medicament label 50 along the tear line 49*b* provided in shield 48 (FIG. 2). This action permits separation of protective shield 48 from cover or cap member 46 in the manner illustrated in FIG. 8. With the component parts in this configuration, the collapsible vial assembly can be mated with the liquid container assembly 14 by inserting externally threaded portion 42 of the vial assembly into the inlet port of the liquid container so that threads 40*a* will mate with threads 28a provided in the inlet port. Rotational forces imparted to cover 46 will then cause base 42 to threadably mate with the inlet port of the container assembly in the manner shown in FIG. 9. In this regard, it is to be noted that top wall 46*d* of cover 46 is provided with an outwardly protruding, generally X-shaped driving protuberance 56 (FIG. 4) which is adapted to be matably received within the X-shaped cavity 40*c* provided in top wall 40*b* of collapsible container 40. It is also to be observed that, as shown in FIG. 5, the periphery of base 42 is provided with a groove 43 which closely receives drive bead 46*c* of cover 46. This drive bead along with driving protuberance 56 imparts a positive rotational movement to base 42 as the cover member 46 is rotated.

With the construction described in the preceding paragraphs, rotational forces imparted upon cover member 46 will cause concomitant rotation of the collapsible vial assembly so as to permit mating of the parts in the manner shown in FIG. 9. As indicated in FIG. 9, as the collapsible vial assembly is mated with the inlet port of container 17, elastomeric plug 32 will move into seating engagement with a generally disk-shaped closure member 58 which initially sealably closes inlet port 20 of container 17 so as to maintain the reservoir thereof in a sterile condition.

With the component parts assembled in the manner shown in FIG. 9, protective cap 46 is removed so as to expose the collapsible container and ready the assemblage for the injection step. By applying a downward force in the direction of the arrow 60 of FIG. 10, wall 40*a* will begin to collapse and elastomeric plug 32 will be caused to move downwardly by stem 34 in the manner indicated by the phantom lines in FIG. 10. As the plug is moved downwardly, disk-like member 58 will be separated from the groove 42*c* which supports it within the inlet port of container assembly 14 and the disk will fall downwardly by force of gravity into the reservoir 18.

Turning to FIG. 13, it can be seen that a continued downward force in the direction of the arrow 60 will cause the support assembly to move from the first position shown in FIG. 10 to the second, ejected position shown in FIG. 13 with elastomeric plug 32 moving outwardly of the inlet port so that the entire support assembly will fall freely by force of gravity into reservoir 18. Once submersed within the liquid contained within container 14, the additive or medicament 36 will controllably separate from the support subassembly and will thoroughly intermix with the liquid "L" contained in reservoir 18.

Following the injection step, it is important to note that the locking means of the invention functions to securely interlock the collapsible vial subassembly with the inlet port of container 17. This locking means is here provided in the form of a plurality of circumferentially spaced-apart locking tabs 66 which are formed on base 42 (FIGS. 6 and 11). Locking tabs 66 are adapted to lockably engage the locking faces 68a of a plurality of circumferentially spaced locking teeth 68 formed proximate the upper periphery of wall 28 of the inlet port of container 17. As indicated in FIG. 11, as the collapsible vial is threadably mated with the inlet port, tab 66 will slide over teeth 68. However, because of the configuration of teeth 68, faces 68*a* of the locking teeth will effectively prevent counter-rotation of the collapsible vial assembly relative to container 17 and in this way preventing delivery adulteration or misuse.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An apparatus for controllably intermixing a first component and a second component comprising:
   - (a) a liquid container having a reservoir for containing the first component, said container including an inlet port and an outlet port;
   - (b) a collapsible vial assembly adapted to be interconnected with said inlet port of said liquid container, said vial assembly including:
     - (i) a base receivable within said inlet port of said liquid container;
     - (ii) a collapsible container connected to said base and extending therefrom, said collapsible container having a collapsible side wall and top wall together defining an internal chamber; and
     - (iii) adding means for presenting said second component to said first component, said adding means comprising a support assembly receivable within said internal chamber and being ejectable therefrom upon collapsing said collapsible wall of said collapsible container, said second component being removably carried by said support assembly.

2. An apparatus as defined in claim 1 in which said base is generally tubular in shape and in which said support assembly of said adding means comprises a generally cylindrically shaped plug receivable within said base.

3. An apparatus as defined in claim 1 further including a protective cover removably connected to said base for enclosing said collapsible wall.

4. An apparatus as defined in claim 1 in which said base of said collapsible vial assembly includes an external connector surface and in which said apparatus further includes a protective shield removably connected to said protective cover for enclosing said external connector surface.

5. An apparatus as defined in claim 1 in which said adding means comprises:
   - (a) a resiliently deformable plug telescopically receivable within said base of said collapsible vial assembly; and
   - (b) an elongated stem extending from said plug, said second component circumscribing said elongated stem.

6. An apparatus as defined in claim 5 in which said adding means further comprises a top connected to said elongated stem, said top being disposed proximate said top wall of said collapsible container.

7. An apparatus as defined in claim 6 in which said side wall of said collapsible container is generally bellows shaped and is collapsible from a first upstanding position to a second foreshortened, collapsed position.

8. An apparatus for controllably intermixing a first component and a second component comprising:
   - (a) a container having a reservoir for containing the first component, said container having an internally threaded, generally tubular shaped inlet port and an outlet port;
   - (b) a collapsible vial assembly adapted to be threadably interconnected with said container, said vial assembly including:
     - (i) an externally threaded, generally tubular shaped base threadably receivable within said inlet port of said container;
     - (ii) a collapsible container connected to said base and extending therefrom, said collapsible container having a collapsible side wall and top wall together defining an internal chamber; and
     - (iii) adding means for presenting said second component to said first component, said adding means being receivable within said internal chamber and being ejectable therefrom upon collapsing said collapsible wall of said collapsible wall.
   - (c) a housing for enclosing said collapsible vial assembly, said housing including:
     - (i) a protective cover removably connected to said base of said collapsible vial assembly for enclosing said collapsible wall; and
     - (ii) a protective shield removably connected to said protective cover for enclosing said base of said collapsible vial assembly.

9. An apparatus as defined in claim 8 in which said adding means comprises:
   - (a) a generally cylindrically shaped, resiliently deformable plug sealably receivable within said base of said collapsible vial assembly;
   - (b) an elongated stem connected to said plug, said second component circumscribing said elongated stem; and
   - (c) a top connected to said elongated stem, said top being disposed proximate said top wall of said collapsible container.

10. An apparatus as defined in claim 9 in which said side wall of said collapsible container is generally bellows shaped and is collapsible from a first upstanding position to a second foreshortened, collapsed position.

11. An apparatus as defined in claim 10 in which said first component comprises a parenteral fluid and in which said second component comprises a beneficial agent.

12. An apparatus as defined in claim 10 in which said top of said adding means is provided with a driving recess and in which said protective cover includes a top wall provided with a driving protuberance receivable within said driving recess.

13. An apparatus as defined in claim 10 further including a medicament label circumscribing a portion of said protective cover and a portion of said protective shield for removably connecting said protective cover to said protective shield.

14. An apparatus for controllably intermixing a first liquid component and a second medicament component comprising:
   - (a) a liquid container having a top, a bottom and spaced-apart sides defining a reservoir for containing the first liquid component, said container having an inlet port and an outlet port;
   - (b) a collapsible vial assembly adapted to be interconnected with said inlet port of said liquid container, said collapsible vial assembly including:
     - (i) a base receivable within said inlet port of said liquid container;
     - (ii) a collapsible container connected to said base and extending therefrom, said collapsible container having a side wall and top wall together defining an internal chamber; and (iii) adding means including a support assembly for supporting the second component, said support assembly being disposed within said internal chamber and being ejectable therefrom upon collapsing said collapsible wall, said adding means further comprising a resiliently deformable plug sealably receivable within said base, an upstanding stem connected to said plug, and a top connected to said upstanding stem, said second component surrounding said upstanding stem; and (c) a housing for housing said collapsible vial assembly, said housing comprising a protective cover surrounding said collapsible wall, said protective cover being removably interconnected with a protective shield surrounding said base of said collapsible vial assembly.

15. An apparatus as defined in claim 14 in which said top of said adding means is provided with a driving recess and in which said protective cover includes a top wall provided with a driving protuberance receivable within said driving recess.

16. An apparatus as defined in claim 14 further including a medicament label circumscribing a portion of said protective cover and a portion of said protective shield for removably connecting said protective cover to said protective shield.

17. An apparatus as defined in claim 14 in which said first component comprises a diluent and in which said second component comprises a beneficial agent.

18. An apparatus as defined in claim 14 in which said first component comprises a solvent and in which said second component comprises a biologically active material drug.

19. An apparatus for controllably intermixing a first component and a second component comprising:

(a) a liquid container having a reservoir for containing the first component, said container including a threaded inlet port and an outlet port;

(b) a collapsible vial assembly having threads engagable with said threaded inlet port of said liquid container, said vial assembly including:

(i) a base receivable within said inlet port of said liquid container;

(ii) a collapsible container connected to said base and extending therefrom, said collapsible container having a generally bellows shaped, collapsible side wall and top wall together defining an internal chamber, said generally bellows shaped, collapsible side wall being collapsible from a first upstanding position to a second foreshortened, collapsed position; and (iii) adding means for presenting said second component to said first component, said adding means being receivable within said internal chamber and being ejectable therefrom upon collapsing said collapsible wall of said collapsible container, said adding means comprising:

a. a resiliently deformable plug telescopically receivable within said base of said collapsible vial assembly;

b. an elongated stem expending from said plug, said second component circumscribing said elongated stem; and c. a top connected to said elongated stem, said top being disposed proximate said top wall of said collapsible container.

20. An apparatus as defined in claim 19 in which said first component comprises a diluent and in which said second component comprises a drug.

* * * * *